(12) United States Patent
Nett et al.

(10) Patent No.: US 12,394,050 B2
(45) Date of Patent: Aug. 19, 2025

(54) HYBRID IMAGING DETECTOR CONFIGURATION FOR COMPUTED TOMOGRAPHY

(71) Applicant: GE Precision Healthcare LLC, Wauwatosa, WI (US)

(72) Inventors: Brian E Nett, Wauwatosa, WI (US); Jonathan S Maltz, Oakland, CA (US); Chad A Smith, Franklin, WI (US); Brandon A. Smith, Waukesha, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 328 days.

(21) Appl. No.: 18/057,184

(22) Filed: Nov. 18, 2022

(65) Prior Publication Data
US 2024/0169521 A1    May 23, 2024

(51) Int. Cl.
*G06T 7/00* (2017.01)
*A61B 6/03* (2006.01)

(52) U.S. Cl.
CPC ............ *G06T 7/0012* (2013.01); *A61B 6/035* (2013.01); *G06T 2207/10081* (2013.01)

(58) Field of Classification Search
None
See application file for complete search history.

(56) References Cited

U.S. PATENT DOCUMENTS

| 6,114,701 A | 9/2000 | Plummer et al. |
| 2011/0080994 A1 | 4/2011 | Hoffman |
| 2012/0057670 A1 | 3/2012 | Luhta |

(Continued)

FOREIGN PATENT DOCUMENTS

| JP | H0810249 A | 1/1996 |
| JP | H09327453 A | 12/1997 |

(Continued)

OTHER PUBLICATIONS

EP application 23205731.5 filed Oct. 25, 2023—Search report issued Apr. 8, 2024; 7 pages.

(Continued)

*Primary Examiner* — Hoon K Song
(74) *Attorney, Agent, or Firm* — McCoy Russell LLP

(57) ABSTRACT

Systems and methods are provided for performing computed tomography (CT) scans using different detector materials within a single CT system. In one embodiment, a CT system comprises a hybrid detector assembly coupled to a rotatable portion of a gantry of the CT system, the hybrid detector assembly including a plurality of detector arrays, the detector arrays separated along a direction parallel to an axis of motion of a table of the CT system, each detector array of the plurality of detector arrays including a different detector material. The hybrid detector assembly may be mounted on a translation mechanism configured to allow a position of the hybrid detector assembly to change within the rotatable portion of the gantry between a first acquisition of projection data and a second acquisition of projection data, to center an x-ray tube on a detector array of the hybrid detector assembly having a desired detector material.

19 Claims, 9 Drawing Sheets

(56) References Cited

U.S. PATENT DOCUMENTS

| | | | |
|---|---|---|---|
| 2015/0223766 A1* | 8/2015 | Besson | G01T 1/2985 |
| | | | 378/62 |
| 2015/0346354 A1* | 12/2015 | Arakita | G06T 11/005 |
| | | | 378/19 |
| 2021/0369219 A1 | 12/2021 | Li | |
| 2022/0042929 A1 | 2/2022 | Zhang | |

FOREIGN PATENT DOCUMENTS

| | | |
|---|---|---|
| JP | 2010124832 A | 6/2010 |
| JP | 2011067524 A | 4/2011 |
| JP | 2012127952 A | 7/2012 |
| JP | 2016097296 A | 5/2016 |

OTHER PUBLICATIONS

JP application 2023-188999 filed Nov. 6, 2023—Office Action issued Nov. 27, 2024; Machine Translation; 6 pages.
JP2010124832 English Abstract; Espacenet.com Feb. 27, 2025; 1 page.
JP application 2023-188999 filed Nov. 6, 2023—Office Action issued Mar. 12, 2025; Machine Translation; 6 pages.
JP2011-067524A English Abstract; Espacenet.com; Jun. 12, 2025.
JP2016-097296A English Abstract; Espacenet.com; Jun. 12, 2025.
JPH08-10249A English Abstract; Espacenet. com; Jun. 12, 2025.
JPH09-327453A English Abstract; Espacenet.com; Jun. 12, 2025.

* cited by examiner

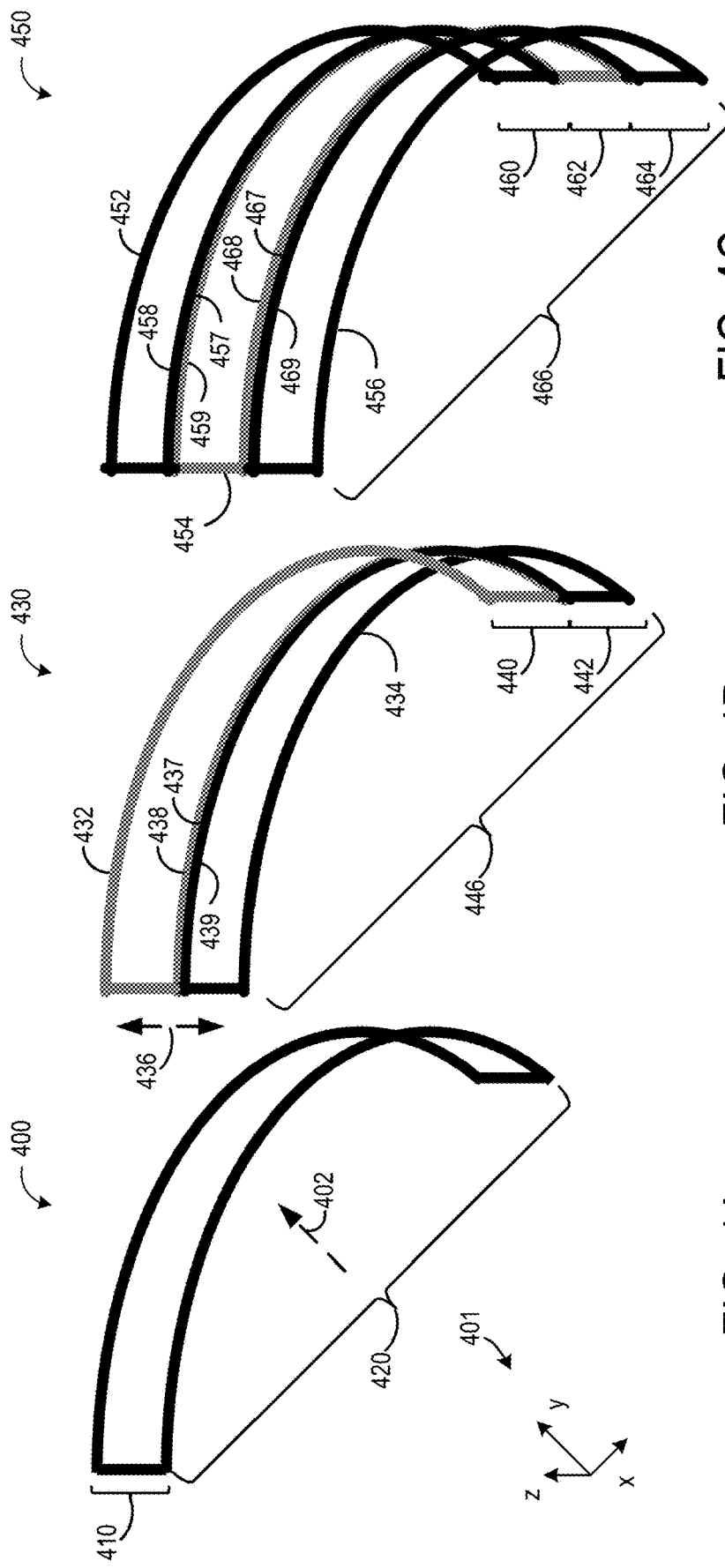

HYBRID IMAGING DETECTOR CONFIGURATION FOR COMPUTED TOMOGRAPHY

TECHNICAL FIELD

Embodiments of the subject matter disclosed herein relate to medical imaging, and more particularly, to increasing a quality of images reconstructed using computerized tomography imaging systems.

BACKGROUND

In computed tomography (CT) imaging systems, an electron beam generated by a cathode is directed towards a target within an x-ray tube. A fan-shaped or cone-shaped beam of x-rays produced by electrons colliding with the target is directed towards a subject, such as a patient. After being attenuated by the object, the x-rays impinge upon an array of radiation detectors, generating an image. Scanners may use different types of detectors, such as conventional indirect-conversion-detector-based Energy Integrating Detectors (EID) or direct-conversion Photon Counting CT (PCCT) detectors, or a different kind of detector.

Scanners purchased by clinics and hospitals typically include one kind of detector. For example, a clinic may purchase a first scanner with EI detectors, or a second scanner with PCCT detectors, but may not purchase both due to financial constraints. Each type of detector may have advantages and disadvantages. EI detectors have a lower cost than PCCT detectors and are sufficient for many imaging tasks. With PCCT detectors, photons are counted to provide spectral information, which may increase a spatial resolution of a reconstructed image. However, photon pile-up may occur at higher input count rates due to a limited capability of the PC detectors, which reduces image quality at a high x-ray flux rate. In general, one type of detector may be more suitable or preferred over another type of detector for an acquisition, depending on desired characteristics of a resulting image. As a result, when purchasing a scanner, the clinics and hospitals may have to weigh trade-offs between different detector types.

SUMMARY

The current disclosure at least partially addresses one or more of the above identified issues by a CT detector system comprising a hybrid detector assembly coupled to a rotatable portion of a gantry of the CT system, the hybrid detector assembly including a plurality of detector arrays, the detector arrays separated along a direction parallel to an axis of motion of a table of the CT system, each detector array of the plurality of detector arrays including a different detector material. The hybrid detector assembly may be slidably mounted within a rotatable portion of a gantry of the CT system, where the rotatable portion rotates around a scanned subject during a scan. In different configurations of the hybrid detector assembly on the gantry, an x-ray tube of the CT system may be centered on different detector arrays. The different configurations may be selected by moving (e.g., sliding) the hybrid detector assembly in a first direction, or in a second, opposite direction, where the first and second directions are parallel to an axis of motion of a table of the CT system (e.g., the z-dimension).

For example, a first detector array with a first detector material may be selected from the plurality of detector arrays to perform an acquisition, based on a first set of desired characteristics of a resulting image. When the first detector array is selected, the hybrid detector assembly may be commanded to move in the first direction, such that the x-ray tube is centered on the first detector array. A second acquisition may be performed, where a second detector array with a second detector material, different than the first detector material, is selected from the plurality of detector arrays, based on a second set of desired characteristics of a resulting image. When the second detector array is selected, the hybrid detector assembly may be moved in the second direction (e.g., the opposite direction), such that the x-ray tube is centered on the second detector array. In other embodiments, the detector assembly may include more than two detector arrays, which may each be centered on the x-ray tube by moving in either of the first or second directions. In this way, a single scanner may be configured to perform either a conventional CT scan, or a PCCT scan. As a result, hospitals and clinics may not have to choose between either a conventional CT scanner and a PCCT scanner, and a wider range of images of different degrees of quality may be supported. Additionally, a size of a PCCT detector array may be reduced, as compared with a typical PCCT detector array of a PCCT scanner, to further decrease a cost of the scanner.

By providing a PCCT detector array within an energy integrating system, some benefits of PCCT may be obtained at a lower cost than purchasing a PCCT scanner. For example, less costly conventional CT scans may be performed when the PCCT functionalities are not desired or cost effective to use, and more costly PCCT scans may be performed when images of a higher quality are desired. For example, a PCCT detector array may be used for tasks, pathologies, or anatomical regions where a higher resolution is desired, and an EI detector array may be used where the higher resolution is not justified. The PCCT detector array may have a reduced field of view, where the PCCT detector may be used on smaller anatomical regions (e.g., heart, extremities) and the EI detector is used for larger anatomical regions. Alternatively, a PCCT detector array may be used primarily for research, while an EI detector array may be used primarily for clinical tasks.

As an additional advantage, a decision regarding which type of detector should be used for a scan may be postponed until a patient is ready to be scanned, whereby an efficiency of scheduling the CT scanner use may be increased, leading to a decreased downtime where resources may not be used.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which:

FIG. 4A is a schematic diagram of a single traditional CT detector, as prior art;

FIG. 4B is a schematic diagram of a first hybrid CT detector assembly, in accordance with one or more embodiments of the present disclosure;

FIG. 4C is a schematic diagram of a second hybrid CT detector assembly, in accordance with one or more embodiments of the present disclosure;

Figure 1:
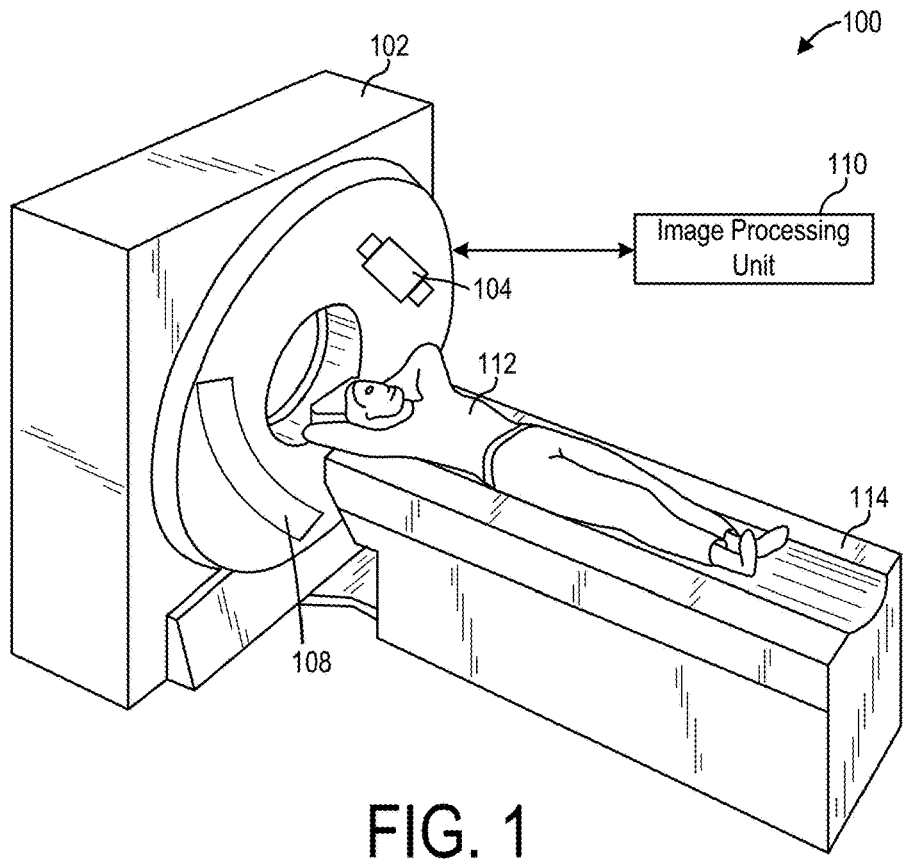
FIG. 1 shows a pictorial view of an imaging system, in accordance with one or more embodiments of the present disclosure.

The drawings illustrate specific aspects of the described systems and methods. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

This description and embodiments of the subject matter disclosed herein relate to methods and systems for increasing a quality of images acquired via a computed tomography (CT) imaging system. In computed tomography (CT) imaging systems, an x-ray source emits a fan-shaped beam or a cone-shaped beam towards an object, such as a patient. Generally, in CT systems the x-ray source and an energy integrating (EI or EID) detector array are rotated about a gantry within an imaging plane and around the patient, and images are generated from projection data at a plurality of views at different view angles. For example, for one rotation of the x-ray source, 1000 views may be generated by the CT system. The beam, after being attenuated by the patient, impinges upon an array of radiation detectors. The x-ray detector or detector array typically includes a collimator for collimating x-ray beams received at the detector, a scintillator disposed adjacent to the collimator for converting x-rays to light energy, and photodiodes for receiving the light energy from the adjacent scintillator and producing electrical signals therefrom. An intensity of the attenuated beam radiation received at the detector array is typically dependent upon the attenuation of the x-ray beam by the patient. Each detector element of a detector array produces a separate electrical signal indicative of the attenuated beam received by each detector element. The electrical signals are transmitted to a data processing system for analysis. The data processing system processes the electrical signals to facilitate generation of an image.

Such conventional CT imaging systems utilize detectors that convert radiographic energy into current signals that are integrated over a time period, then measured and ultimately digitized. However, a drawback of such detectors is their inability to provide data or feedback as to the number and/or energy of photons detected. That is, the light emitted by the scintillator is a function of both a number of x-rays impinged and an energy level of the x-rays. The photodiodes may not be capable of discriminating between the energy level or the photon count from the scintillation. For example, two scintillators may illuminate with equivalent intensity and, as such, provide equivalent output to their respective photodiodes. Yet, despite yielding an equivalent light output, the number of x-rays received by each scintillator may be different, and an intensity of the x-rays may be different.

In contrast, PCCT detectors may provide photon counting and/or energy discriminating feedback with high spatial resolution. PCCT detectors can be caused to operate in an x-ray counting mode, an energy measurement mode of each x-ray event, or both. While a number of materials may be used in the construction of a hybrid photon counting energy discriminating detector, semiconductors have been shown to be one preferred material. Typical materials for such use include Cadmium Zinc Telluride (CZT), Cadmium Telluride (CdTe), Gallium Arsenide, Perovskites, and Silicon (Si), which have a plurality of pixilated anodes attached thereto.

As PCCT detectors support energy measurement or tagging in addition to x-ray photon counting, the acquisition of both anatomical detail as well as tissue characterization information is supported. In this regard, energy discriminating information or data may be used to reduce the effects of beam hardening and the like. Furthermore, these detectors support the acquisition of tissue discrimination data and therefore provide diagnostic information that is indicative of disease or other pathologies. PCCT detectors can also be used to detect, measure, and characterize materials that may be injected into a subject, such as contrast agents and/or other specialized materials, by the use of optimal energy weighting to boost the contrast of iodine and calcium (and other high atomic-number materials). Contrast agents can, for example, include iodine that is injected into the blood stream for increased contrast during visualization.

However, one drawback of direct conversion semiconductor detectors, however, is that these types of detectors cannot count at the x-ray photon fluxes typically encountered with conventional CT systems. Saturation and pile-up can occur at detector locations where small subject thickness is interposed between the detector and the radiographic energy source or x-ray tube. Pile-up is a phenomenon that occurs with PCCT detectors when a source flux at the detector is so high that there is a non-negligible possibility that two or more x-ray photons deposit charge packets in a single pixel close enough in time so that their signals interfere with each other. These events may be recognized as one single event having the sum of their energies, with the events shifted in the spectrum to higher energies. In addition, pile-up leads to a more or less pronounced depression of counts in high x-ray flux, resulting in detector quantum efficiency (DQE) loss. This pile-up may lead to detector saturation, which occurs at a relatively low x-ray flux level in direct conversion sensors. Above the level, the detector response is not predictable and has degraded dose utilization that leads to loss of imaging information and results in noise and artifacts in x-ray projection and CT images.

Thus, EI detectors and PCCT detectors each have advantages and disadvantages. For some clinical tasks, EI detectors may be preferred, and for other clinical tasks, PCCT detectors may be preferred, depending on desired image characteristics. In other words, EI detectors may offer a first set of advantages, and PCCT detectors may offer a second set of advantages, where selecting one kind of detector may entail sacrificing the advantages of the other kind of detector. For example, PCCT detectors may generate higher quality images than EI detectors in a central portion of a scanned object, and EI detectors may generate higher quality images at portions on a side of the scanned object (e.g., due to pile-up).

To provide healthcare workers and facilities the ability to benefit from advantages of different kinds of detectors within a single CT system, the inventors herein have proposed a novel approach for switching between detector types (e.g., detector materials) within the single CT system, where a plurality of different detector types may be assembled on a gantry in a movable fashion. A detector assembly including the plurality of different detector types may be moved to center an electron beam emanating from an x-ray source on a desired detector type of the plurality of different detector types.

Figure 2:
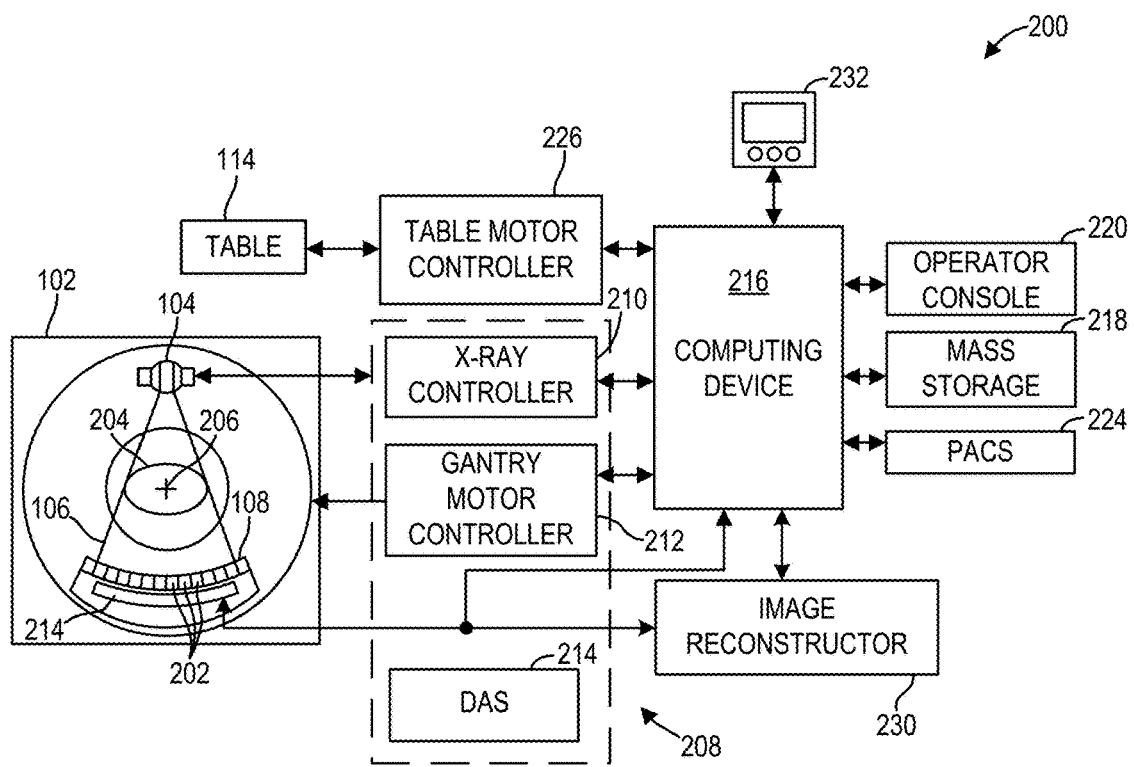
FIG. 2 shows a block schematic diagram of an exemplary imaging system, in accordance with one or more embodiments of the present disclosure.
Figure 3:
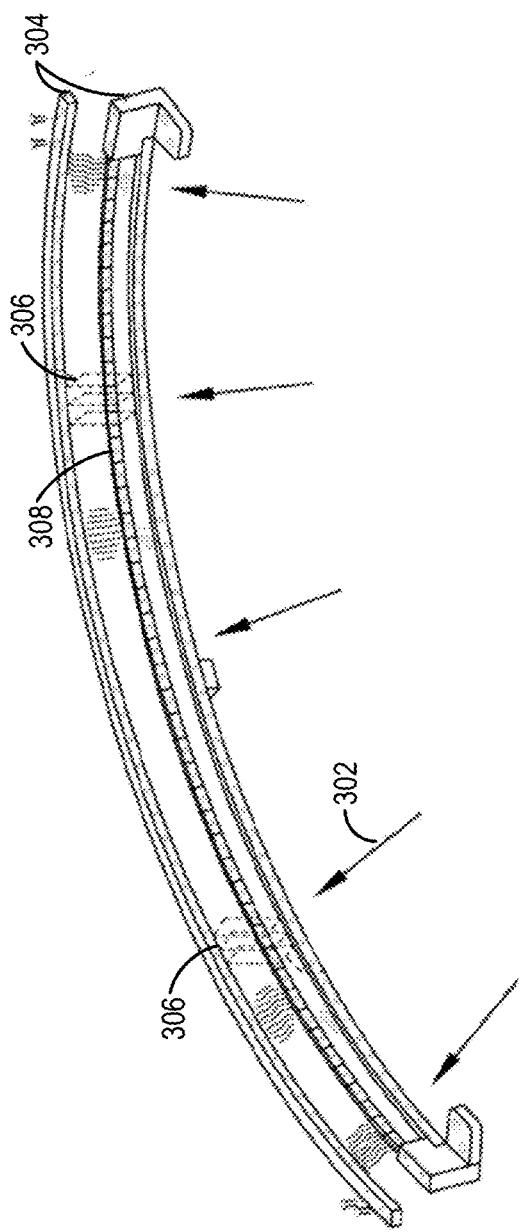
FIG. 3 is a schematic diagram of an exemplary detector array of a CT system, in accordance with one or more embodiments of the present disclosure.
Figure 5A:
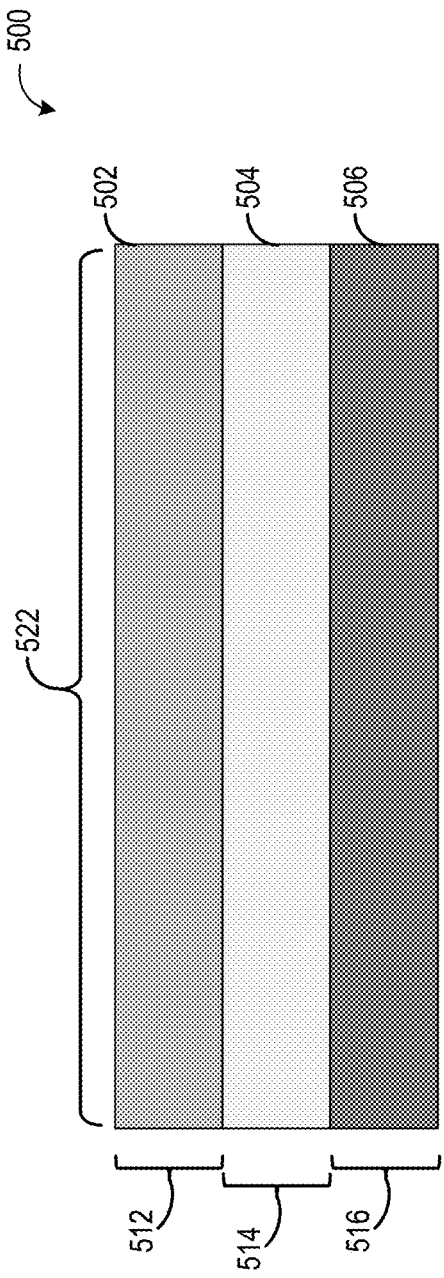
FIG. 5A is a schematic diagram showing a first configuration of detector arrays of a hybrid CT detector assembly, in accordance with one or more embodiments of the present disclosure.
Figure 5B:
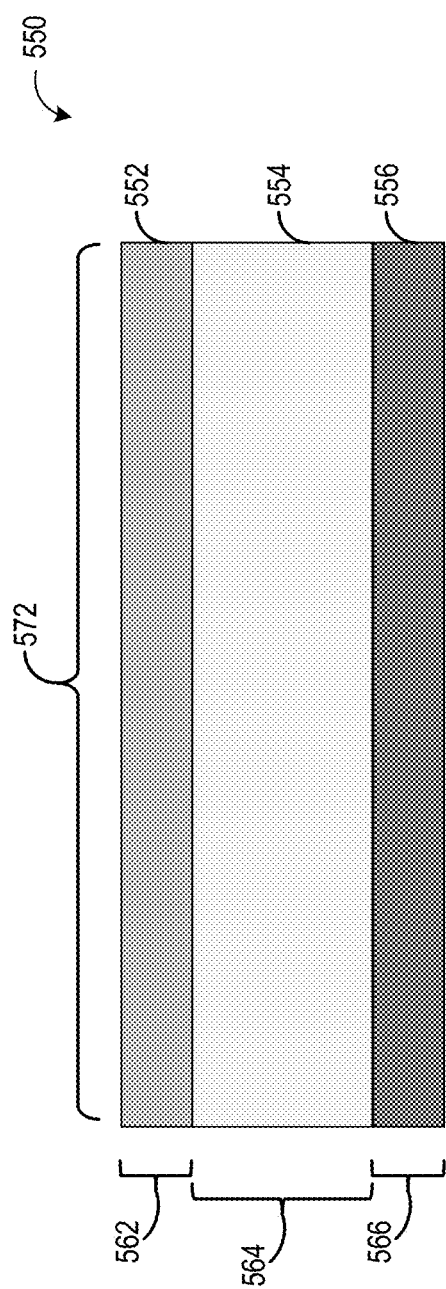
FIG. 5B is a schematic diagram showing a second configuration of detector arrays of a hybrid CT detector assembly, in accordance with one or more embodiments of the present disclosure.
Figure 6A:
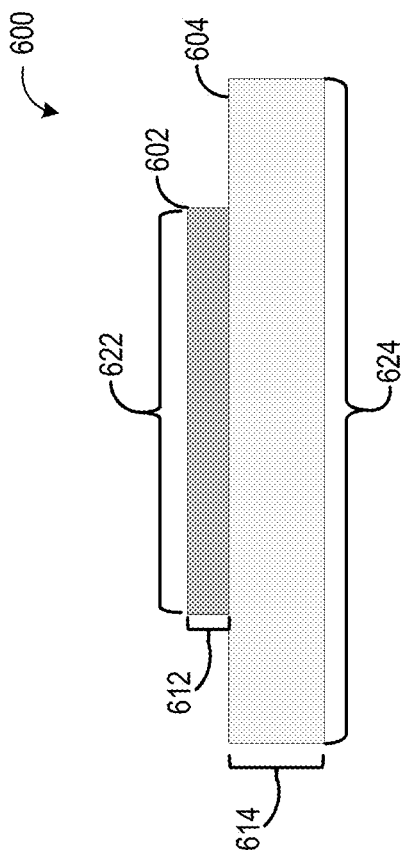
FIG. 6A is a schematic diagram showing a third configuration of detector arrays of a hybrid CT detector assembly, in accordance with one or more embodiments of the present disclosure.
Figure 6B:
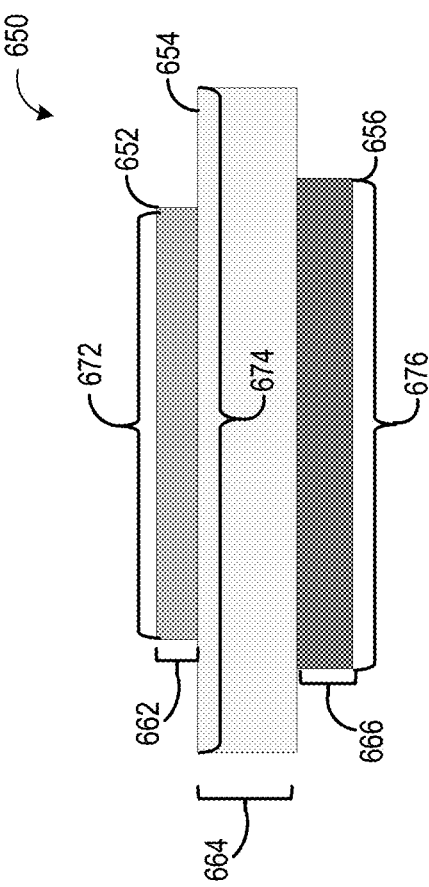
FIG. 6B is a schematic diagram showing a fourth configuration of detector arrays of a hybrid CT detector assembly, in accordance with one or more embodiments of the present disclosure.
Figure 7A:
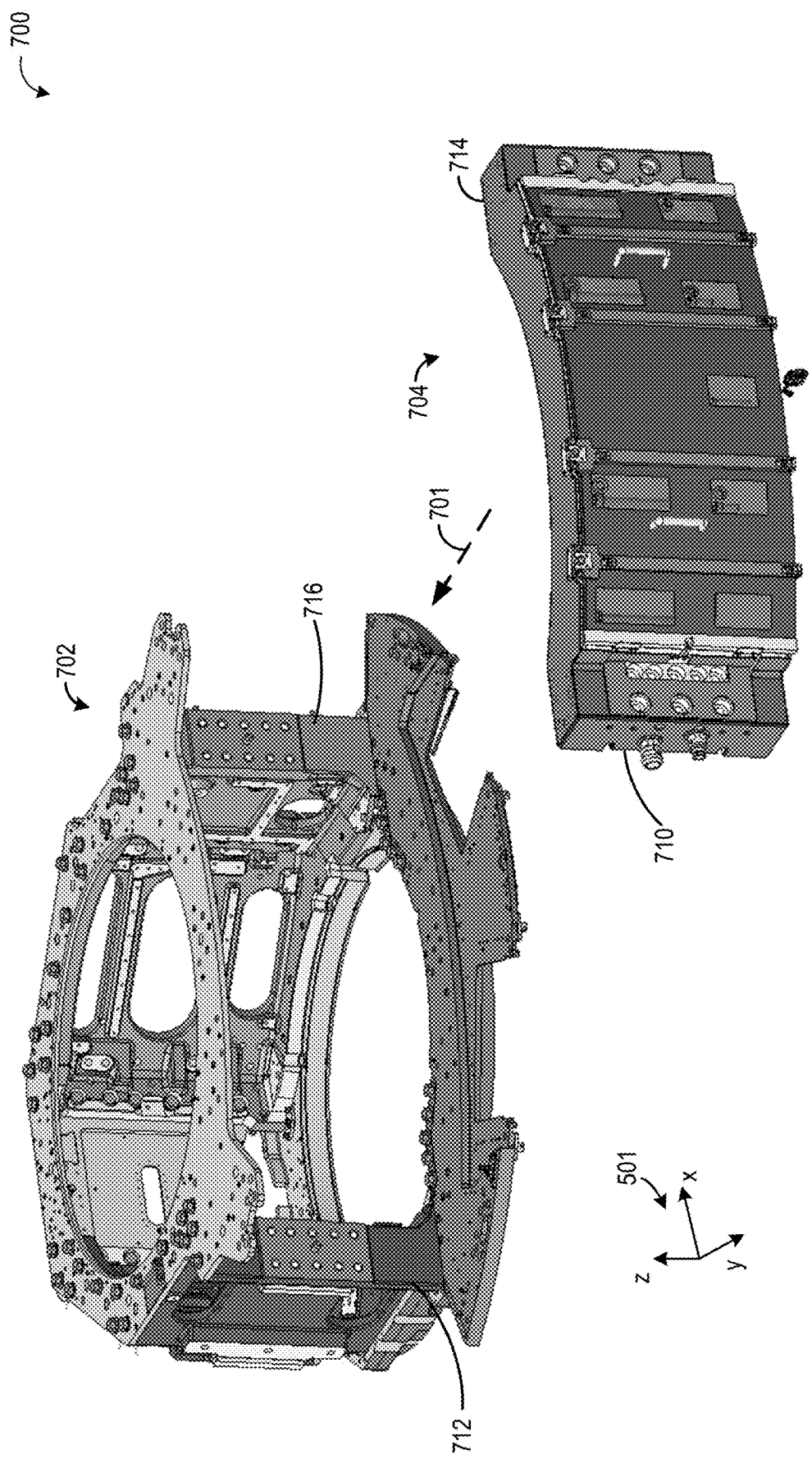
FIG. 7A shows a rotatable portion of a gantry including a mountable hybrid CT detector assembly in a first orientation, in accordance with one or more embodiments of the present disclosure.
Figure 7C:
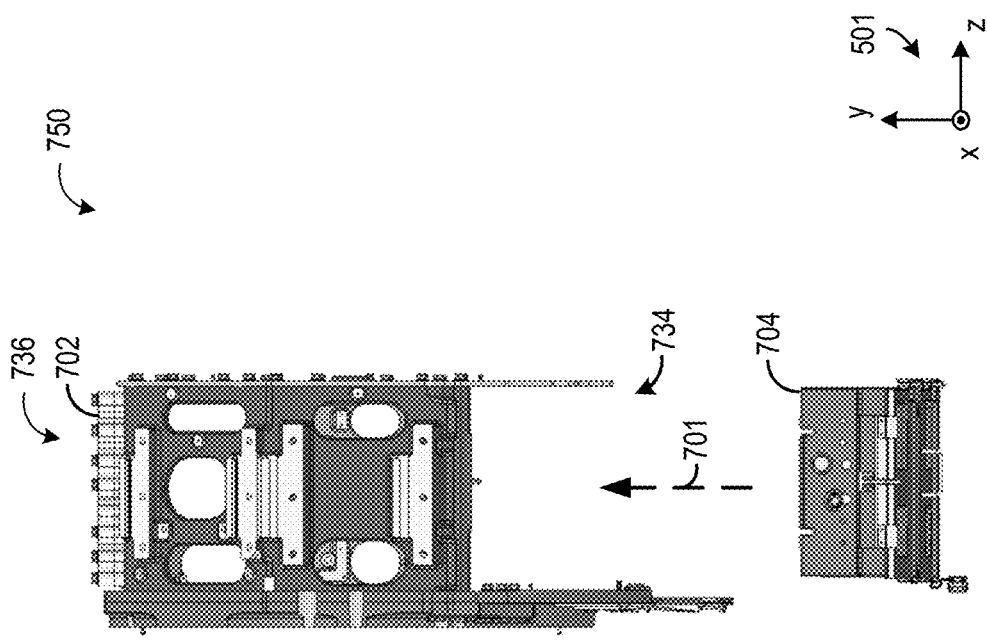
FIG. 7C shows a rotatable portion of a gantry including a mountable hybrid CT detector assembly in a third orientation, in accordance with one or more embodiments of the present disclosure.
Figure 7B:
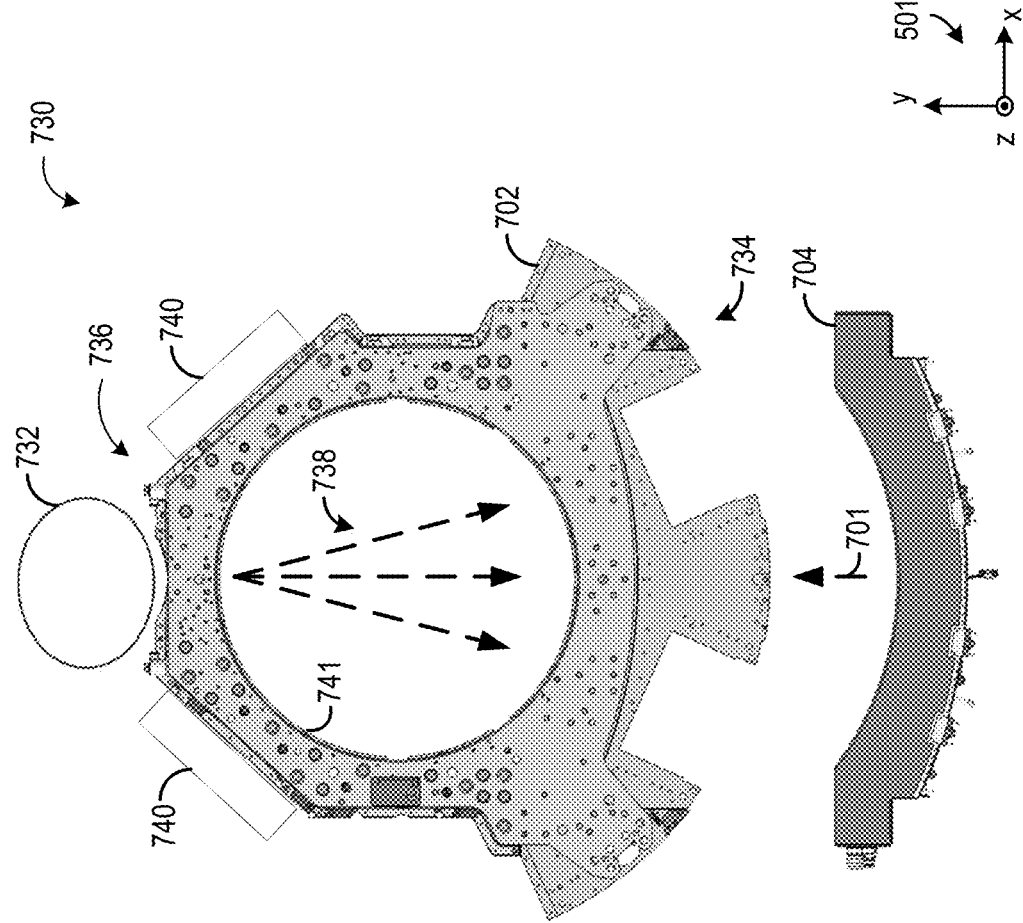
FIG. 7B shows a rotatable portion of a gantry including a mountable hybrid CT detector assembly in a second orientation, in accordance with one or more embodiments of the present disclosure.

An example of a CT system that may be used to perform scans in accordance with the present techniques is provided in FIGS. 1 and 2. FIG. 3 and FIG. 4A show example CT detector arrays of the CT system. Different types of CT detector arrays may be arranged in a movable hybrid CT detector assembly, as shown in FIGS. 4B and 4C. FIG. 5A shows a first configuration of a movable hybrid CT detector assembly including three CT detector arrays, where each detector array has a different detector type or material. A relative size of the detector arrays in the movable hybrid CT detector assembly may vary, where some detector arrays may be larger (e.g., have a greater extent in one or more dimensions) than other detector arrays, as shown in FIGS. 5B, 6A, and 6B. The movable hybrid CT detector assemblies may be coupled to a gantry as shown in FIGS. 7A, 7B, and 7C. Prior to a scan, the hybrid CT detector assembly may be adjusted from a first position shown in FIG. 7D, where x-ray beams are focused on a first detector array of a movable hybrid CT detector assembly, to a second position shown in FIG. 7E, where the x-ray beams are focused on a second detector array of the movable hybrid CT detector assembly. Switching between different detector arrays of a movable hybrid CT detector assembly may be performed by following a method shown in FIG. 8.

FIGS. 1-7E show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below/underneath one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example. Additionally, FIGS. 7A-7E are shown to scale. However, other dimensions may be used.

FIG. 1 illustrates an exemplary CT system 100 configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation for use in imaging the subject 112 laying on a table 114. Specifically, the x-ray source 104 is configured to project the x-ray radiation beams towards a detector array 108 positioned on the opposite side of the gantry 102. Although FIG. 1 depicts a single x-ray source 104, in certain embodiments, multiple x-ray sources and detectors may be employed to project a plurality of x-ray radiation beams for acquiring projection data at different energy levels corresponding to the patient. In some embodiments, the x-ray source 104 may enable dual-energy gemstone spectral imaging (GSI) by rapid peak kilovoltage (kVp) switching. In the embodiments described herein, the x-ray detector employed is a photon-counting detector which is capable of differentiating x-ray photons of different energies.

In certain embodiments, the CT system 100 further includes an image processing unit 110 configured to reconstruct images of a target volume of the subject 112 using an iterative or analytic image reconstruction method. For example, the image processing unit 110 may use an analytic image reconstruction approach such as filtered back projection (FBP) to reconstruct images of a target volume of the patient. As another example, the image processing unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processing unit 110 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z Cartesian coordinate system and generally referred to as an "imaging volume." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of an x-ray radiation beam by the object. Each detector element of the array produces a separate electrical signal that is a measurement of the x-ray beam attenuation at the detector location. The attenuation measurements from all the detector elements are acquired separately to produce a transmission profile.

In some CT systems, the x-ray source and the detector array are rotated with a gantry within the imaging plane and around the object to be imaged such that an angle at which the x-ray beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray radiation beam that passes through the subject 204 (such as a patient) to acquire a corresponding projection data. In some embodiments, the detector array 108 may be fabricated in a multi-slice configuration including the plurality of rows of cells or detector elements 202, where one or more additional rows of the detector elements 202 are arranged in a parallel configuration for acquiring the projection data. The detector elements 202 may also be referred to as pixels or detector pixels.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections. In some examples, the individual detectors or detector elements 202 of the detector array 108 may include photon-counting detectors which register the interactions of individual photons into one or more energy bins.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a 3D volumetric image of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors. The data sampled and digitized by the DAS 214 is transmitted to a computer or computing device 216. It is noted that the computing device 216 may be the same or similar to image processing unit 110, in at least one example. In one example, the computing device 216 stores the data in a storage device or mass storage 218. The storage device 218, for example, may be any type of non-transitory memory and may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

Referring now to FIG. 3, a CT detector array 300 is shown, which may be a non-limiting example of detector array 108 of FIG. 2. Detector array 300 includes rails 304 having collimating blades or plates 306 placed therebe-tween. Plates 306 are positioned to collimate x-rays 302 before such beams impinge upon a plurality of detector modules 308 of detector array 300, which may be arranged between the plates 306. As an example, detector array 300 may include 57 detector modules 308, each detector module 308 having an array size of 64×16 of detector (e.g., pixel) elements. As a result, detector array 300 would have 64 rows and 912 columns (16x57 detectors), allowing for 64 simultaneous slices of data to be collected with each gantry rotation (e.g., the gantry 102 of FIG. 1).

Different types of detector elements may be used. The CT detector modules 308 may include EID detectors configured to indirectly convert radiographic energy to electrical signals via photodiodes receiving the light energy from adjacently positioned scintillators. Alternatively, the CT detector modules 308 may include PCCT detectors configured to directly convert radiographic energy to electrical signals containing energy discriminatory or photon count data. For example, when a photon impinges upon a detector element of a PCCT detector module 308, a charge may be generated within a semiconductor layer of the detector element that is proportional to the energy of the photon. A comparator may compare the voltage of the generated charge to one or more thresholds and increment a count of a bin (of a plurality of bins) based on the voltage relative to the one or more thresholds. The plurality of bins may include 8 bins, for example, with energy thresholds configured for optimal material decomposition performance.

As described below in reference to FIGS. 4A, 4B, and 4C, a plurality of CT detector arrays 300 may be coupled together in a CT detector assembly mounted on a gantry of a CT system (e.g., gantry 102 of CT system 100).

FIG. 4A shows a traditional CT detector array 400, which may be a non-limiting example of CT detector array 300 of FIG. 3. CT detector array 400 is typically rigidly mounted on the gantry, and not moved between imaging acquisitions. CT detector array 400 may include different types of detector modules and detector elements. For example, a first CT detector array 400 may include EI detectors; a second CT detector array 400 may include PCCT detectors; and one or more additional CT detector arrays 400 may include different kinds of detectors. While CT detector array 400 is depicted as a detector arc (e.g., having a curved shape), in other embodiments, CT detector array 400 may be flat. For example, the CT system may be a flat-panel imaging system, and CT detector array 400 may include direct or indirect flat panel imaging detectors. For example, the CT system may be used for interventional and radiation therapy.

CT detector array 400 has an extent (e.g., a height) 410 in a direction parallel to a motion of a table of the CT system, referred to herein as a z-dimension, as shown on reference axes 401. (It should be appreciated that for descriptive purposes, the extents of CT detector array 400 and other components described herein in various dimensions are described herein as heights, lengths, or widths based on an orientation depicted in the figures). CT detector array 400 has a length 420 extending in a direction perpendicular to a motion of a table of the CT system, in an x-dimension, as shown on reference axes 401. Either or both of height 410 and length 420 may vary depending on the CT system, such that a surface area of CT detector array 400 on which an x-ray projected in a direction 402 (e.g., the y-dimension) is focused may be customized depending on an implementation.

FIG. 4B shows a simplified view of a first hybrid detector assembly 430, where first hybrid detector assembly 430 includes a first detector array 432, and a second detector array 434. First detector array 432 and second detector array 434 may be non-limiting examples of CT detector array 300 and/or CT detector array 400. First detector array 432 and second detector array 434 may include different types of detector modules and detector elements. For example, first detector array 432 may include EI detectors, and second detector array 434 may include PCCT detectors; or first detector array 432 may include PCCT detectors, and second detector array 434 may include EI detectors; or either or both of first detector array 432 and second detector array 434 may include a different type of detector.

First detector array 432 and second detector array 434 may be arranged adjacently in face-sharing contact in first hybrid detector assembly 430 at a junction 437, where a bottom edge 438 of first detector array 432 meets a top edge 439 of second detector array 434 (e.g., in the z-dimension indicated by arrow 436). In some embodiments, first detector array 432 may be coupled to second detector array 434 at junction 437. In other embodiments, first detector array 432 may not be coupled to second detector array 434 at junction 437, and both first detector array 432 and second detector array 434 may be coupled to the gantry such that first detector array 432 and second detector array 434 are in face-sharing contact at junction 437. In yet other embodiments, first detector array 432 and second detector array 434 may both be coupled to a structural component of first hybrid detector assembly 430, and the structural component may be coupled to the gantry. In still other embodiments, bottom edge 438 of first detector array 432 and top edge 439 of second detector array 434 may not be in face sharing contact with each other, where first detector array 432 and second detector array 434 may be separated by a space, or a component that acts as a physical divider.

In various embodiments, first hybrid detector assembly 430 may be mounted on a translation mechanism coupled to the gantry, such that first hybrid detector assembly 430 may be moved on the gantry between acquisitions, in the direction indicated by an arrow 436 (e.g., the z-dimension, normal to a direction of the x-rays). For example, the translation mechanism may be a set of rails arranged on the gantry, and first hybrid detector assembly 430 may slide along the set of rails. Specifically, first hybrid detector assembly 430 may slide along the rails from a first position at which x-rays are centered on first detector array 432, to a second position at which x-rays are centered on second detector array 434. At each position, a locking mechanism may lock first hybrid detector assembly 430 in place, such that first hybrid detector assembly 430 may not move during an acquisition. For example, the locking mechanism may be coupled to first hybrid detector assembly 430, and may include a pin that slidably engages with a hole in the rails or gantry. Alternatively, the locking mechanism may include a clutch and braking mechanism, such that the clutch is engaged at a desired position, and disengaged when sliding between positions. At the first position, projection data may be acquired by detector elements of first detector array 432, and at the second position, projection data may be acquired by detector elements of second detector array 434. An example of a hybrid detector assembly sliding from a first position to a second position is described in further detail below in reference to FIGS. 7D and 7E.

Alternatively, in some embodiments, first hybrid detector assembly 430 may be coupled to the gantry at a fixed location, and an x-ray source (e.g., an x-ray tube) may be mounted on the translation mechanism, such that the x-ray source may be moved on the gantry between acquisitions, in the direction indicated by the arrow 436 (e.g., the z-dimension). In other words, while first hybrid detector assembly 430 and other hybrid detector assemblies described herein are described as being moved to center the x-ray source on a desired detector array, a similar result may be obtained by fixing the position of the hybrid detector assembly and adjusting a position of the x-ray source.

First detector array 432 has a first height 440, and second detector array 434 has a second height 442. First height 440 may be the same as second height 442, or first height 440 may be the different from second height 442. First height 440 and second height 442 may depend on a type of semiconductor material (e.g., detector type) of first detector array 432 and second detector array 434, respectively. For example, first detector array 432 may include EI detectors, and second detector array 434 may include PCCT detectors. Due to a higher cost of the PCCT detectors with respect to the EIDs, a surface area of second detector array 434 may be smaller than a surface area of first detector array 432, whereby height 440 may be greater than height 442. Alternatively, first detector array 432 may include PCCT detectors, and second detector array 434 may include EI detectors, and height 440 may be less than height 442.

First detector array 432 has a length 446, which may be the same as length 420 of FIG. 4A. Second detector array 434 is shown as also having length 446. However, in different embodiments, first detector array 432 and second detector array 434 may have different lengths.

FIG. 4C shows a simplified view of a second hybrid detector assembly 450, where second hybrid detector assembly 450 includes a first detector array 452, a second detector array 454, and a third detector array 456, each of which may be the same as or similar to detector array 300. First detector array 452, second detector array 454, and third detector array 456 may include the same or different types of detector modules and detector elements (EI detectors, PCCT detectors, and/or a different type of detector). For example, in a first embodiment, first detector array 452 may include PCCT detectors; second detector array 454 may include EI detectors; and third detector array 456 may include PCCT detectors. In a second embodiment, first detector array 452 may include EI detectors; second detector array 454 may include a first configuration of PCCT detectors; and third detector array 456 may include a second configuration of PCCT detectors. In a third embodiment, first detector array 452 may include PCCT detectors; second detector array 454 may include a first configuration of EI detectors; and third detector array 456 may include a second configuration of EI detectors. In general, second hybrid detector assembly 450 may include detectors of various types in various configurations.

As described above in reference to FIG. 4B, in second hybrid detector assembly 450, first detector array 452 and second detector array 454 may be arranged adjacently in face-sharing contact at a junction 457, where a bottom edge of first detector array 452 meets a top edge of second detector array 454 (e.g., in the z-dimension). Second detector array 454 and third detector array 456 may be arranged adjacently in face-sharing contact at a junction 467, where a bottom edge of second detector array 454 meets a top edge of third detector array 456 (e.g., in the z-dimension). As with first hybrid detector assembly 430, first detector array 452, second detector array 454, and third detector array 456 may be coupled to each other at one or more of junctions 457 and 467, and/or first detector array 452, second detector array 454, and third detector array 456 may be coupled to a structural component of second hybrid detector assembly 450 holding first detector array 452, second detector array 454, and/or third detector array 456 in face-sharing contact, or first detector array 452, second detector array 454, and third detector array 456 may be coupled to the gantry. In some embodiments, bottom edge 458 of first detector array 452 and top edge 459 of second detector array 434 may not be in face sharing contact with each other and may be separated by a space or a component acting as a divider, and/or bottom edge 468 of second detector array 454 and top edge 469 of third detector array 456 may not be in face sharing contact with each other and may be separated by a space or a component acting as a divider.

Second hybrid detector assembly 450 may be mounted on a translation mechanism coupled to the gantry (e.g., rails), such that second hybrid detector assembly 450 may be moved with respect to the gantry to center x-rays emanating from an x-ray source of the CT system on one of first detector array 452, second detector array 454, and third detector array 456.

First detector array 452 has a first height 460, second detector array 454 has a second height 462, and third detector array 456 has a third height 464. As described above in reference to FIG. 4B, first height 460, second height 462, and/or third height 464 may be the same or different, depending on various factors, including operational demands and relative costs of semiconductor material. First detector array 452, second detector array 454, and third detector array 456 are shown as having a length 466. However, in different embodiments, first detector array 452, second detector array 454, and third detector array 456 may have different lengths.

In some embodiments, a first detector array may be fixed to the gantry, while additional detector arrays may be arranged in a hybrid detector assembly configured to move relative to the first, fixed detector array. For example, second hybrid detector assembly 450 may include first detector array 452 and third detector array 456, where first detector array 452 and third detector array 456 are separated by a space of the size of second detector array 454, and second detector array 454 may be fixed to the gantry on an opposite side of second hybrid detector assembly 450 with respect to the x-ray source in the y-dimension (e.g., behind second hybrid detector assembly 450). In a first position of second hybrid detector assembly 450, x-rays may pass through second hybrid detector assembly 450 (e.g., through the space separating first detector array 452 and third detector array 456) and impinge on second detector array 454. For a subsequent scan where a different detector type is desired, second hybrid detector assembly 450 may be moved in a first direction along the z-dimension to a second position, where the x-rays impinge on first detector array 452, or second hybrid detector assembly 450 may be moved in a second direction along the z-dimension to a third position, where the x-rays impinge on third detector array 456. In other words, second hybrid detector assembly 450 may be moved such that either of first detector array 452 and third detector array 456 obscures second detector array 454, and no x-rays impinge on second detector array 454, or second hybrid detector assembly 450 may be moved such that neither of first detector array 452 and third detector array 456 obscures second detector array 454, whereby the x-rays impinge on second detector array 454. In other examples, different configurations of first detector array 452, second detector array 454, and third detector array 456 may be used in fixed or moveable positions. One advantage of including a fixed-position detector array is that an overall size of the gantry may be reduced. Another advantage of including a fixed-position detector array is that a weight of second hybrid detector assembly 450 may be reduced, which may increase an efficiency or speed of moving second hybrid detector assembly 450.

FIG. 5A shows a first example configuration 500 of detector arrays of a hybrid detector assembly of a CT system, such as second hybrid detector assembly 450 of FIG. 4C. First example configuration 500 includes a first detector array 502, a second detector array 504, and a third detector array 506, which may be non-limiting examples of first detector array 452, second detector array 454, and third detector array 456. First detector array 502 includes detector elements of a first detector type; second detector array 504 includes detector elements of a second detector type, and third detector array 506 includes detector elements of a third detector type. The first detector type, the second detector type, and the third detector type may be different from each other, or may include the same or similar detectors in a different configuration or size. In FIG. 5A, first detector array 502, second detector array 504, and third detector array 506 are depicted as flat panel detector arrays. However, in other embodiments, first detector array 502, second detector array 504, and third detector array 506 may be curved detector arrays, as described above in reference to FIGS. 3 and 4A-4C. In FIG. 5A, In FIG. 5A, in the z-dimension indicated in reference axes 501, first detector array 502 has a height 512, second detector array 504 has a height 514, and third detector array 506 has a height 516, where heights 512, 514, and 516 are equal. Additionally, first detector array 502, second detector array 504, and third detector array 506 share an equal length 522 (e.g., in the x-dimension). As such, first detector array 502, second detector array 504, and third detector array 506 may have an equal surface area.

In contrast, FIG. 5B shows a second example configuration 550 of detector arrays of a hybrid detector assembly of the CT system, including a first detector array 552, a second detector array 554, and a third detector array 556. First detector array 552 may include detector elements of the first detector type; second detector array 554 may include detector elements of the second detector type; and third detector array 556 may include detector elements of the third detector type.

In FIG. 5B, first detector array 552, second detector array 554, and third detector array 556 share an equal length 522, in the x-dimension indicated in reference axes 501. However, first detector array 552 has a height 562 (e.g., in the z-dimension), second detector array 554 has a height 564, and third detector array 556 has a height 566, where heights 562, 564, and 566 are not equal. As such, first detector array 502, second detector array 504, and third detector array 506 may not have an equal surface area. Specifically, height 564 is greater than heights 562 and 566, whereby second detector array 554 is depicted as having a greater surface area than first detector array 552 and third detector array 556.

In other words, relative sizes of first detector array 552, second detector array 554, and third detector array 556 may be advantageously configured or adjusted to meet various goals. For example, second detector array 554 may include EI detectors, which are less costly to produce and use and which may provide high quality images in a majority of scans. First detector array 552 may include PCCT detectors, which are more expensive and may not be relied on as frequently as the EI detectors. Third detector array 556 may include a different detector type, which may not be used as frequently as second detector array 554. As a result of second detector array 554 being less costly to produce and use, and being used more frequently than first detector array 552 and third detector array 556, the surface area of second detector array 554 may be increased, while the surface area of first detector array 552 and third detector array 556 may be decreased. By increasing the surface area of second detector array 554, a quality of images reconstructed from projection data acquired via second detector array 554 may be increased. A reduced surface area of first detector array 552 and/or third detector array 556 may not result in a decreased quality of images reconstructed from first detector array 552 and/or third detector array 556. However, the reduced surface area may increase an amount of time used to scan a subject. Additionally, the reduced surface area may result in first detector array 552 and/or third detector array 556 being used to scan a smaller region of interest of a scanned subject. Thus, by adjusting relative heights of different detector arrays in a hybrid detector assembly, a scanner may support performing scans using detectors of different types while meeting performance and cost targets.

FIG. 6A shows a third example configuration 600 of two detector arrays of a hybrid detector assembly of a CT system, such as first hybrid detector assembly 430 of FIG. 4B. Third example configuration 600 includes a first detector array 602 and a second detector array 604, which may be non-limiting examples of first detector array 432 and second detector array 434. First detector array 602 may include detector elements of a first detector type, and second detector array 504 may include detector elements of a second detector type. For example, the first detector type may be a PCCT detector, and the second detector type may be an EI detector.

In the z-dimension indicated in reference axes 501, first detector array 602 has a height 612, and second detector array 604 has a height 614, where height 614 is greater than height 612. Additionally, first detector array 602 has a length 622 (e.g., in the x-dimension), and second detector array 604 has a length 624, which is greater than length 622. As such, first detector array 602 has a smaller surface area than second detector array 604.

In some embodiments, first detector array 602 may have a lesser height and/or length than detector array 604 due to a relative expense of a detector material of detector array 602 with respect to detector array 604. For example, detector array 602 may include a first semiconductor material that is more expensive than a second semiconductor material of detector array 604, and detector array 602 may have a shorter height or length than detector array 604 to reduce an overall cost of the CT system. Additionally or alternatively, height 612 may be based on manufacturing limitations of detector array 602. For example, a detector material (e.g., silicon) may be manufactured at some sizes, but not manufactured at other, larger sizes, or a cost of manufacturing the detector material at larger sizes may be cost prohibitive. If a detector material cannot be manufactured with a desired extent in at least one dimension, height 612 may be shortened to an extent at which the at least one dimension that can be manufactured. In other embodiments, height 612 may be reduced as a result of space constraints resulting from a limited total extent of the hybrid detector assembly and/or gantry on which the hybrid detector assembly is mounted in the z-dimension.

FIG. 6B shows a fourth example configuration 650 of three detector arrays of a hybrid detector assembly, such as second hybrid detector assembly 450 of FIG. 4C. Fourth example configuration 650 includes a first detector array 652, a second detector array 654, and a third detector array 656, which may be non-limiting examples of first detector array 452, second detector array 454, and third detector array 456, respectively. First detector array 652 includes detector elements of a first detector type; second detector array 654 includes detector elements of a second detector type, and third detector array 656 includes detector elements of a third detector type, which may be different from each other. In various embodiments, the first detector type may include a first detector material, the second detector type may include a second detector material, and the third detector type may include a third detector material. For example, the first detector type may include PCCT detector elements; the second detector type may include EI detector elements; and the third detector type may be used for flat-panel imaging, for example, for mammography for interventional x-ray imaging tasks.

Alternatively, one or more of the first detector type, the second detector type, and the third detector type may include the same or similar detectors in a different configuration, size, thickness, and/or extent in one or more dimensions. For example, the first detector type may include PCCT detector elements; the second detector type may include an EI detector array and/or EI detector elements of a first size, and the third detector type may include an EI detector array and/or EI detector elements of a second size, or a composite EI detector array including EI detector elements of different thicknesses (e.g., sandwiched arrays). In other embodiments, the first detector type may include PCCT detector elements; the second detector type may include EI detector elements of a first thickness, and the third detector type may include EI detector elements of a second thickness. It should be appreciated that the examples provided herein are for illustrative purposes, and the different types may be differentiated in various ways without departing from the scope of this disclosure.

In fourth example configuration 650, in the z-dimension indicated in reference axes 501, first detector array 652 has a height 662, second detector array 654 has a height 664, and third detector array 656 has a height 666, where heights 662, 664, and 666 are different. Additionally, first detector array 652 has a length 672 (e.g., in the x-dimension), second detector array 654 has a length 674, and third detector array 656 has a length 676, where lengths 672, 674, and 676 are different. Specifically, height 662 is less than height 666, and both height 662 and length 666 are less than height 664, and length 672 is less than length 676, and both length 672 and length 676 are less than length 674. As such, first detector array 652, second detector array 654, and third detector array 656 may have different surface areas. As described above, the different surface areas may be configured to maximize or minimize various properties of the CT system and/or images reconstructed from the CT system. For example, first detector array 652 may be a first PCCT detector array; second detector array 654 may be an EI detector array; and third detector array 656 may be a second PCCT detector array. The surface areas of first detector array 652 and third detector array 656 may be decreased to reduce a cost of the CT system, and the surface area of second detector array 654 may be increased to increase a quality of images reconstructed from the EI detectors of second detector array 654, which may be used more frequently than the PCCT detectors of first detector array 652 and third detector array 656.

A relative positioning of detector arrays within a hybrid detector assembly may be advantageously based on one or more characteristics of different detector arrays. For example, the relative positioning of the detector arrays may be based on an anticipated usage of one or more detector arrays of the hybrid detector assembly, where a first detector array with a high anticipated usage may be centered in the z-dimension, and other detector arrays may be positioned around the first detector array (e.g., depicted in FIGS. 5A-6B as being above or below the first detector array in the z-dimension). Additionally, in a default or starting position of the CT system, the x-ray source may be centered on the first detector array, such that the hybrid detector assembly may not be moved for an acquisition using the first detector array, and the hybrid detector assembly may be moved for an acquisition using detector arrays with a lower anticipated usage. In this way, the movement of the hybrid detector assembly with respect to a gantry of the CT system may be minimized, reducing a wear on the hybrid detector assembly and/or a frequency of maintenance of the hybrid detector assembly, and increasing a useful life of the hybrid detector assembly and/or components of the gantry coupling with the hybrid detector assembly (e.g., a rail). In other embodiments, the relative positioning of the detector arrays may be based on one or more additional or different characteristics of the detector arrays, such as, for example, a relative weight and/or a size of the detector arrays. For example, the detector arrays may be arranged within the hybrid detector assembly to minimize a total distance moved by the hybrid detector assembly over a plurality of scans.

FIG. 7A shows a schematic diagram 700 of a rotatable portion 702 of a gantry of a CT system, such as gantry 102 of CT system 100 of FIG. 1, and a mountable hybrid CT detector assembly 704, from a first perspective with respect to the set of reference axes 501. Mountable hybrid CT detector assembly 704 may be a non-limiting example of hybrid detector array assemblies 430 and 450 shown in a simplified manner in FIGS. 4B and 4C, and may include detector arrays of different types in various configurations such as those described above in reference to FIGS. 5A-6B. Mountable hybrid CT detector assembly 704 may be mechanically coupled to rotatable portion 702, in a y-dimension of reference axes 501 as indicated by directional arrow 701. In various embodiments, a first inner surface 710 of mountable hybrid CT detector assembly 704 may be bolted to a first outer surface 712 of rotatable portion 702, and a second inner surface 714 of mountable hybrid CT detector assembly 704 may be bolted to a second outer surface 716 of rotatable portion 702.

FIG. 7B shows a schematic diagram 730 of rotatable portion 702 and mountable hybrid CT detector assembly 704 from a second perspective with respect to reference axes 501 (e.g., in the x/y dimensions). Schematic diagram 730 shows a coupling of mountable hybrid CT detector assembly 704 to rotatable portion 702 at a first side 734 of rotatable portion 702, where an x-ray source 732 of the CT system is positioned at a second, opposing side 736 of rotatable portion 702. As such, x-rays generated by x-ray source 732 may be directed as indicated by arrows 738 at one of a plurality of detector arrays arranged (e.g., stacked in the z-dimension) in mountable hybrid CT detector assembly 704.

As described in greater detail below in reference to FIGS. 7D and 7E, mountable hybrid CT detector assembly 704 may include a plurality of movable detector arrays, where a position of the detector arrays may be adjusted in the z-dimension to center the x-rays on a desired detector array of the plurality of movable detector arrays. (As described above, in some embodiments, the detector arrays may be fixed, and the x-ray source (e.g., x-ray source 732) may be adjusted in the z-dimension to center the x-rays on the desired detector array.) When the detector arrays are shifted from a first position to a second position, a distribution of weight throughout mountable hybrid CT detector assembly 704 and rotatable portion 702 may be altered, generating an imbalance that may affect a rotation of rotatable portion 702. In some embodiments, the imbalance may be addressed by decreasing a speed of rotation of rotatable portion 702. In other embodiments, the change in the distribution of weight may be offset by coupling one or more movable weights 740 to second, opposing side 736 of rotatable portion 702. The one or more movable weights 740 may be configured such that when the detector arrays shift position, the one or more movable weights 740 are moved to compensate for the change in the distribution of weight. For example, if the detector arrays are moved in a first direction in the z-dimension, the one or more movable weights 740 may be moved in a second, opposite direction in the z-dimension to compensate. An ability of the one or more movable weights 740 to compensate for the movement of the detector arrays may depend on a size of the one or more movable weights 740. If the one or more movable weights 740 are small, the movement of the detector arrays may be partially compensated for. When the movement of the detector arrays is partially compensated for, the speed of rotation of rotatable portion 702 may be reduced to mitigate a resulting imbalance. Alternatively, the one or more movable weights 740 may be sized to fully compensate for the movement of the detector arrays, whereby the speed of rotation of rotatable portion 702 may not be reduced. In some embodiments, a size of rotatable portion 702 may be increased to make room for larger sized weights. Alternatively, in some embodiments, the one or more moveable weights 740 may be positioned at or coupled to an inner bore 741 of rotatable portion 702.

FIG. 7C shows a schematic diagram 750 of rotatable portion 702 and mountable hybrid CT detector assembly 704, from a third perspective with respect to reference axes 501 (e.g., in the y/z dimensions). Schematic diagram 730 shows the coupling of mountable hybrid CT detector assembly 704 to rotatable portion 702 at first side 734 of rotatable portion 702, in the y-dimension indicated by arrow 701.

Figure 7E:
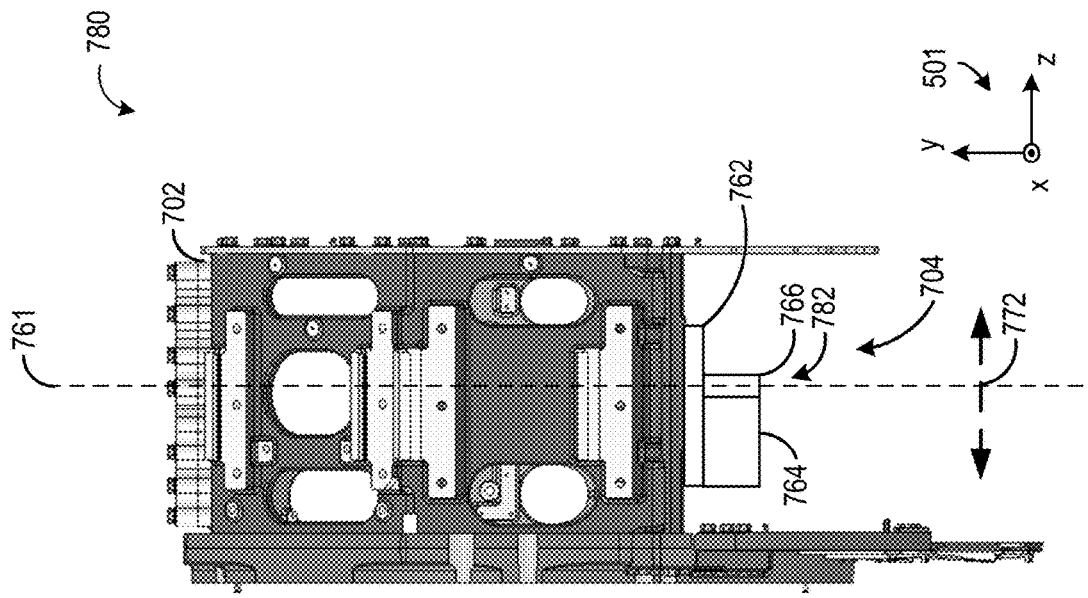
FIG. 7E shows the mountable hybrid CT detector assembly of FIGS. 7A-7C in a second configuration, in accordance with one or more embodiments of the present disclosure.
Figure 7D:
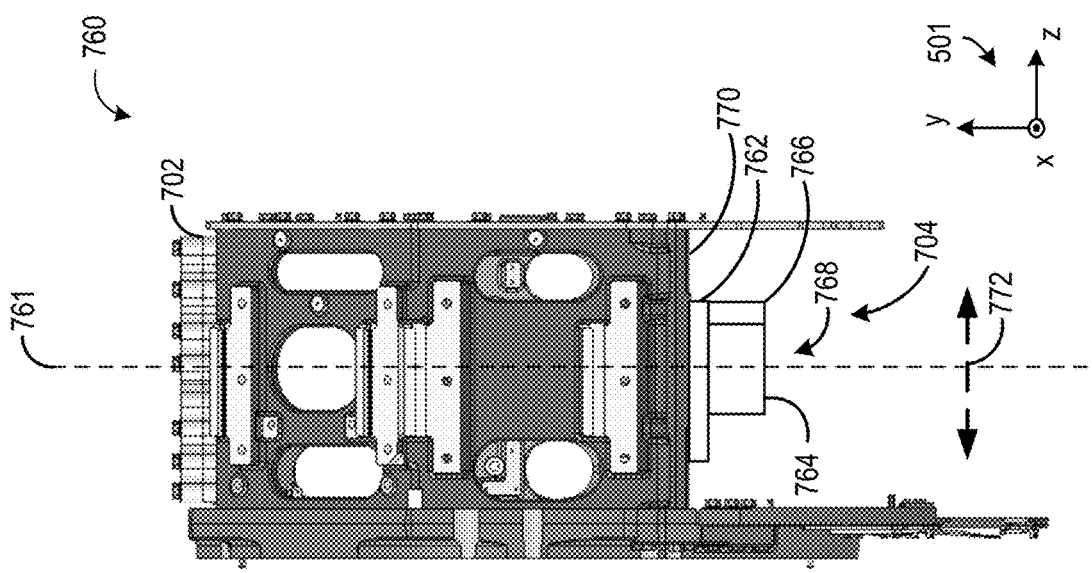
FIG. 7D shows the mountable hybrid CT detector assembly of FIGS. 7A-7C in a first configuration, in accordance with one or more embodiments of the present disclosure.

FIG. 7D shows a schematic diagram 760 of rotatable portion 702 of FIGS. 7A, 7B, and 7C from the third perspective of FIG. 7C with respect to reference axes 501 (e.g., in the y/z dimensions). Schematic diagram 760 includes a simplified view of mountable hybrid CT detector assembly 704, showing a rail 762, a first detector array 764, and a second detector array 766. First detector array 764 and second detector array 766 may be non-limiting examples of first detector array 602 and second detector array 604, respectively. For example, first detector array 764 may be an EID detector array including EI detector elements, and second detector array 766 may be a PCCT detector array including PCCT detector elements. First detector array 764 and second detector array 766 may be coupled together as described above in reference to FIG. 6A, either to each other directly or to a shared component of mountable hybrid CT detector assembly 704. It should be further appreciated that mountable hybrid CT detector assembly 704 and/or parts and/or portions of mountable hybrid CT detector assembly 704 may be sized differently depending on a number of detector arrays included in mountable hybrid CT detector assembly 704.

In various embodiments, rail 762 may be mechanically coupled to a bottom side 770 (in the depicted y-dimension) of rotatable portion 702, in a fixed position. First detector array 764 and second detector array 766 may be slidably coupled to rail 762, such that first detector array 764 and second detector array 766 may slide along rail 762 in the z-dimension, indicated by a directional arrow 772. In FIG. 7D, first detector array 764 and second detector array 766 are shown in a first position 768 with respect to rotatable portion 702, where first detector array 764 is centered and aligned with a center of a scan plane indicated by dashed line 761. As a result of first detector array 764 being centered and aligned with the center of the scan plane, x-rays generated by x-ray source 732 may impinge on detector elements of first detector array 764, and may not impinge on detector elements of second detector array 766. Thus, projection data may be acquired from first detector array 764 and not from second detector array 766, and a CT image may be reconstructed from the projection data acquired via first detector array 764.

FIG. 7E shows a schematic diagram 780 of rotatable portion 702 and the simplified view of mountable hybrid CT detector assembly 704, where first detector array 764 and second detector array 766 are shown in a second position 782 with respect to rotatable portion 702, where second detector array 766 is centered and aligned with the center of a scan plane indicated by dashed line 761. As a result of second detector array 766 being centered and aligned with the center of the scan plane, x-rays generated by x-ray source 732 may impinge on detector elements of second detector array 766, and may not impinge on detector elements of first detector array 764. Thus, projection data may be acquired from second detector array 766 and not from first detector array 764, and a CT image may be reconstructed from the projection data acquired via second detector array 766.

In other words, mountable hybrid CT detector assembly 704 may be advantageously switched between first position 768 and the second position 782 depending on whether a scan is desired to be performed using projection data from first detector array 764, or projection data from second detector array 766. When projection data from first detector array 764 is desired, first detector array 764 and second detector array 766 may be slid along rail 762 in a first direction (e.g., to the left in FIGS. 7D and 7E) along the z-dimension indicated by arrow 772. When projection data from second detector array 766 is desired, first detector array 764 and second detector array 766 may be slid along rail 762 in a second, opposite direction (e.g., to the right in FIGS. 7D and 7E) along the z-dimension indicated by arrow 772. In this way, the CT system may be configured to scan a subject using detectors of different types.

For example, the mountable hybrid CT detector assembly 704 may be switched to the first position 768 to perform a first acquisition of projection data from a first subject. For the first acquisition, a radiologist may wish to perform a scan using EI detectors, which may be faster and may use resources more efficiently than other types of detectors, and from which reconstructed images of high quality may be generated. After the first acquisition has been completed, the radiologist may wish to perform a second acquisition. For the second acquisition, the radiologist may wish to perform a scan using PCCT detectors, which may generate a higher quality reconstructed image than may be obtained from the EI detectors. To perform the second acquisition, the mountable hybrid CT detector assembly 704 may be switched from first position 768 to second position 782, whereby second detector array 766 may be positioned in the center of the scan plane indicated by dashed line 761. As a result of second detector array 766 being positioned in the center of the scan plane, projection data may be acquired by second detector array 766 including the PCCT detectors, and an image may be reconstructed from the projection data.

Figure 8:
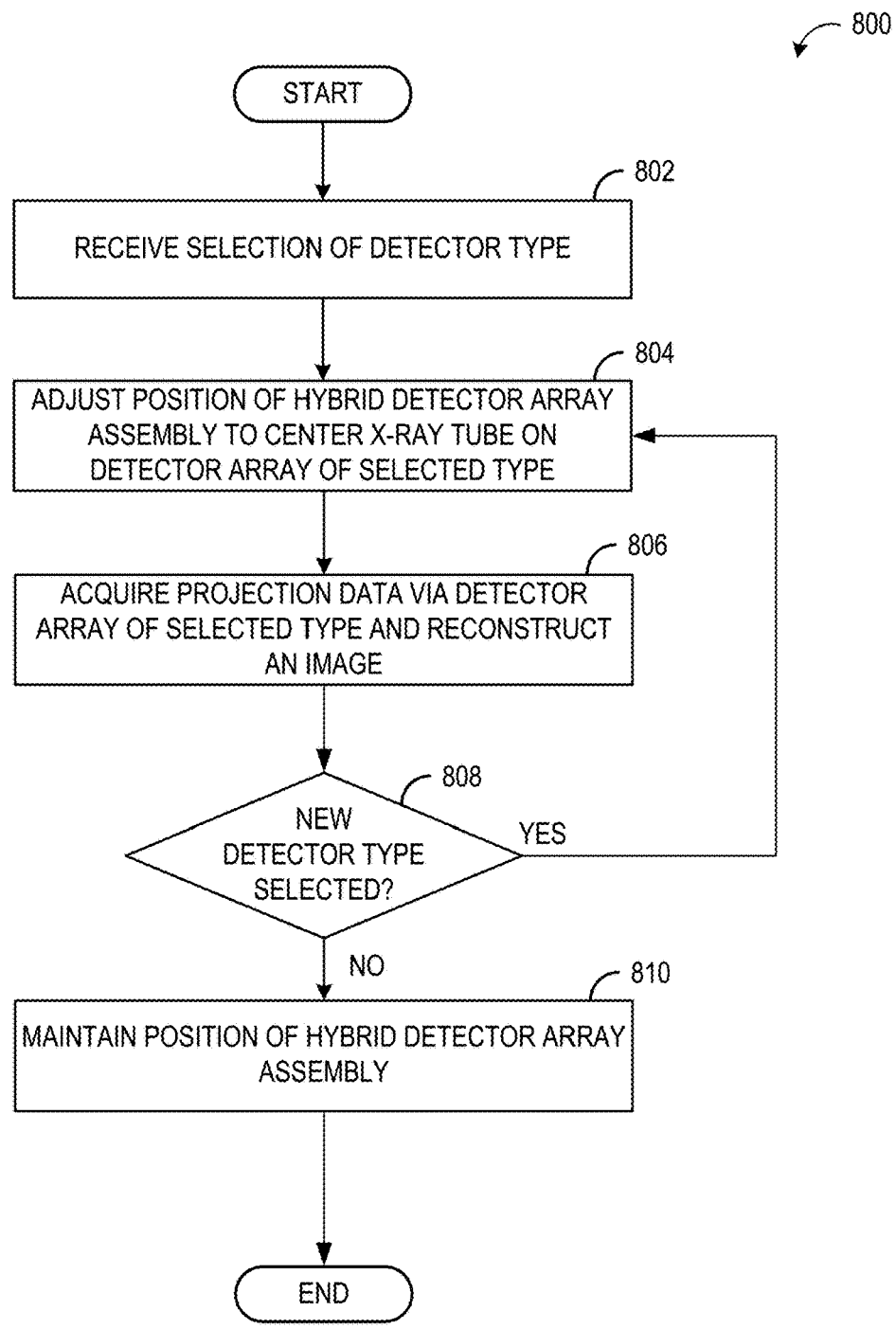
FIG. 8 is a flowchart illustrating an exemplary method for switching between different detector arrays between acquisitions of a CT system, in accordance with one or more embodiments of the present disclosure.

Referring now to FIG. 8, a flowchart is shown illustrating an exemplary method 800 for switching between different detector arrays of a hybrid CT detector assembly of a CT imaging system, such as mountable hybrid CT detector assembly 704 of FIGS. 7A-7E. Method 800 may be stored as instructions in a non-transitory memory and executed by one or more processors of a computing device of the CT imaging system, such as computing device 216 of imaging system 200 of FIG. 2.

Method 800 begins at 802, where method 800 includes receiving a selection of a type of detector that is desired to be used in a CT scan. In various embodiments, the detector type may be selected based on one or more desired characteristics of an image reconstructed from projection data acquired via the selected detector type.

As an example, a first type of detector may be an EI detector, which may be selected if a conventional CT image is desired. A second type of detector may be a PCCT detector, which may be selected if an image with a higher spatial resolution than a conventional CT image is desired. For example, a conventional CT image may be desired based on a desired speed of image reconstruction, where a conventional CT image may be reconstructed more rapidly than an image reconstructed from PCCT detector data. Reconstructing a conventional CT image from EID data may also consume less computational and memory resources than reconstructing an image from PCCT data, where a potential increase in image quality from using the PCCT data may not justify the increased amount of time, processing power, and memory relied on for reconstructing an image from the PCCT data. Alternatively, for some imaging tasks, the increased amount of time, processing power, and memory of using PCCT data may be justified, whereby the PCCT detector type may be selected.

The desired detector type may be selected by a user of the CT system, such as a radiologist, a doctor, a technician, or a different healthcare provider. In various embodiments, the desired detector type may be selected by the user via a graphical user interface of the CT system displayed on a display device of the CT system (e.g., display device 232 of FIG. 2). Further, the desired detector type may be selected by the user at a time of performing a scan using the CT system. For example, the user may scan a subject using a first configuration of the CT system where EID detectors are used to acquire projection data, to generate a conventional CT image. After reviewing the conventional CT image, the user may reconfigure the CT system to select a different detector type (e.g., a PCCT detector), to perform a second scan of the subject, where a resulting image may be of a higher quality.

At 804, method 800 includes adjusting a position of a hybrid CT detector assembly of the CT system to center an x-ray tube of the CT system on a detector array of the selected detector type. The hybrid CT detector assembly may be the same as or similar to the hybrid CT detector assemblies described in reference to FIGS. 4B-7E. For example, adjusting the position of the hybrid CT detector assembly may include sliding a plurality of detector arrays (e.g., first detector array 764 and second detector array 766) along a rail (e.g., rail 762) in a first direction, or a second, opposing direction along a z-dimension of the CT system (e.g., aligned with a motion of a table of the CT system on which a scanned subject is positioned), as described above in reference to FIGS. 7D and 7E.

At 806, method 800 includes acquiring projection data via the selected detector array, and generating an image from the acquired projection data. The image, and/or 2D slices of the image may be displayed on the display device. In one example, x-rays are directed toward the selected detector type only after the x-ray tube is centered with the selected detector array.

At 808, method 800 includes determining whether a new detector type has been selected. For example, the user may wish to perform a subsequent acquisition, on the same subject or on a different subject, where the subsequent acquisition is performed using a different detector type than the first acquisition. Additionally or alternatively, the imaging may be completed, and additional imaging may not be desired. In some embodiments, the detector type may be defined or suggested by a scan protocol implemented. For example, a first scan protocol may specify that a first detector type is desired, or may suggest that the user select the first detector type; a second scan protocol may specify that a second detector type is desired, or may suggest that the user select the second detector type; and so on. A specification of a detector type in a scan protocol may be made, for example, by a human expert prior to a time of performing a scan. In some cases, a specification of a detector type may be made at least partially based on a machine learning algorithm trained to predict a suitable detector type for a corresponding imaging task.

If at 808 it is determined that a new detector type has been selected for the subsequent scan, method 800 proceeds back to 804, where the position of the hybrid detector assembly is adjusted to center the x-ray tube on a detector array including the newly selected detector type, to acquire an image with projection data acquired from the selected detector type. X-rays may no longer be directed toward the hybrid detector array until the newly selected detector type is centered with the x-ray tube. During this process, the patient may remain in the imaging system. By doing this, a single imaging system may be used to acquire CT images of multiple types.

Alternatively, if at 808 it is determined that a new detector type has not been selected for a subsequent scan, method 800 proceeds to 810. At 810, method 800 includes maintaining the current position of the hybrid detector assembly, and method 800 ends.

Thus, methods and systems are provided herein for performing CT scans using different detector types or materials within a single CT system. The CT system may include a hybrid detector assembly comprising various detector arrays of the different materials, which may be stacked in the z-dimension (e.g., parallel to an axis of motion of a table of the CT system) such that a position of the hybrid detector assembly in the z-dimension may be shifted between acquisitions to center an x-ray tube of the CT system on a desired detector array having a desired detector type/material. A first image may be reconstructed using projection data acquired during a first acquisition using a first detector array (e.g., an EI detector array), and a second image may be reconstructed using projection data acquired during a second acquisition using a second, different detector array (e.g., a PCCT detector array). A user of the CT system may select a desired detector type/material at a time of a scan, to move the hybrid detector assembly into a position where the desired detector array is centered on the x-ray tube. By allowing the user to decide on a type of acquisition to perform at a time of a scan, a use of the CT system may be scheduled more efficiently, resulting in an increased usage rate. By providing different detector capabilities within a single system, clinics and hospitals can perform different types of scans without having to purchase additional equipment, saving costs. As a result, hospitals and clinics may not have to choose between either a conventional CT scanner and a PCCT scanner, and a wider range of images of different degrees of quality may be supported.

The technical effect of providing detector arrays of different detector materials within a CT system is that a wider range of types of reconstructed images may be supported, at a lower cost than purchasing different CT systems for the different types of reconstructed images.

The disclosure also provides support for a computed tomography (CT) system, comprising a hybrid detector assembly coupled to a rotatable portion of a gantry of the CT system, the hybrid detector assembly including a plurality of detector arrays, the detector arrays separated along a direction parallel to an axis of motion of a table of the CT system, each detector array of the plurality of detector arrays including a different detector material. In a first example of the system, the plurality of detector arrays includes an energy integrating (EI) detector array and a photon counting (PC) detector array. In a second example of the system, optionally including the first example, at least one of the hybrid detector assembly and an x-ray tube of the CT system is mounted on a translation mechanism configured to allow a position of the at least one of the hybrid detector assembly and the x-ray tube to change within the rotatable portion of the gantry between a first acquisition of projection data and a second acquisition of projection data. In a third example of the system, optionally including one or both of the first and second examples, the translation mechanism includes a rail. In a fourth example of the system, optionally including one or more or each of the first through third examples, the translation mechanism includes a locking mechanism to lock the hybrid detector assembly in a desired position during an acquisition. In a fifth example of the system, optionally including one or more or each of the first through fourth examples, the system further comprises: a processor, and a non-transitory memory including instructions that when executed by the processor, cause the at least one of the hybrid detector assembly and the x-ray tube to move from a first position, where the x-ray tube is centered on a first detector array of the plurality of detector arrays, the first detector array used for the first acquisition of projection data, to a second position where the x-ray tube is centered on a second detector array of the plurality of detector arrays, the second detector array used for the second acquisition of projection data. In a sixth example of the system, optionally including one or more or each of the first through fifth examples, the at least one of the hybrid detector assembly and the x-ray tube is moved in the direction parallel to the axis of motion of the table of the CT system. In a seventh example of the system, optionally including one or more or each of the first through sixth examples, the first detector array is an energy integrating detector (EID) array, and a conventional CT image is generated from the first acquisition of projection data, and the second detector array is a photon-counting computed tomography (PCCT) detector array, and an image based on PCCT data is generated from the second acquisition of projection data. In a eighth example of the system, optionally including one or more or each of the first through seventh examples, a detector array of the plurality of detector arrays is selected by a user of the CT system to perform an acquisition based on at least one of: one or more desired characteristics of an image reconstructed from projection data obtained during the acquisition, a desired time frame for reconstructing the image, and an amount of computing and/or memory resources available during the acquisition. In a ninth example of the system, optionally including one or more or each of the first through eighth examples, the plurality of detector arrays are arranged in an adjacent manner, where each detector array of the plurality of detector arrays is in face-sharing contact with neighboring detector arrays in the hybrid detector assembly. In a tenth example of the system, optionally including one or more or each of the first through ninth examples, a detector material of the different detector materials cannot be manufactured with a desired extent in at least one dimension. In a eleventh example of the system, optionally including one or more or each of the first through tenth examples, an extent of two or more detector arrays of the plurality of detector arrays in the direction parallel to the axis of motion of the table is not equal. In a twelfth example of the system, optionally including one or more or each of the first through eleventh examples, a first detector array of the two or more detector arrays is an EID array, a second detector array of the two or more detector arrays is a PCCT array, and a surface area of the EID array is greater than the surface area of the PCCT array. In a thirteenth example of the system, optionally including one or more or each of the first through twelfth examples, a field of view of two or more detector arrays of the plurality of detector arrays is not equal. The disclosure also provides support for a method for a computed tomography (CT) imaging system, the method comprising: receiving, from a user of the CT system, a first selection of a first detector type from a plurality of detector types of the CT imaging system, adjusting a position of a hybrid detector assembly including a plurality of detector arrays, each detector array of the plurality of detector arrays having a different detector type, from a first position within a rotatable portion of a gantry of the CT system to a second position within the rotatable portion of the gantry, the second position centering an x-ray source of the CT system on a first detector array of the first detector type, scanning a subject using the first detector array, reconstructing an image of the subject based on projection data acquired via the first detector array. In a first example of the method, the detector type is based on at least one of: a semiconductor material of a detector array, and a surface area of the detector array. In a second example of the method, optionally including the first example, the method further comprises: receiving from the user a second selection of a second detector type from the plurality of detector types, the second detector type different from the first detector type, adjusting the position of the hybrid detector assembly from the second position within the rotatable portion of the gantry to a third position within the rotatable portion of the gantry, the third position centering the x-ray source on a second detector array of the second detector type, scanning a subject using the second detector array, reconstructing an image of the subject based on projection data acquired via the second detector array. In a third example of the method, optionally including one or both of the first and second examples, adjusting the position of the hybrid detector assembly further comprises: sliding the hybrid detector assembly along a translation mechanism of the CT imaging system from the first position to the second position, and locking the hybrid detector assembly in the second position. The disclosure also provides support for a computed tomography (CT) imaging system, comprising: a hybrid detector assembly coupled to a rotatable portion of a gantry of the CT system, the hybrid detector assembly including a plurality of detector arrays, the detector arrays separated along a direction parallel to an axis of motion of a table of the CT system, each detector array of the plurality of detector arrays including a different detector material, a processor, and a non-transitory memory including instructions that when executed by the processor, cause the CT system to: in a first condition, where the hybrid detector assembly is in a first position, the first position centering an x-ray source of the CT system on a first detector array of the plurality of detector arrays, the first detector array having a desired detector material: scan a subject using the first detector array, and reconstruct a first image of the subject based on projection data acquired via the first detector array, and in a second condition, where the hybrid detector assembly is in the first position centering the x-ray source on the first detector array, the first detector array not having the desired detector material: move the hybrid detector assembly to a second position, the second position centering the x-ray source on a second detector array, the second detector array having the desired detector material, and scan the subject using the second detector array, and reconstruct a second image of the subject based on projection data acquired via the second detector array. In a first example of the system, the first position and the second position are two points along a dimension parallel to the axis of motion of the table.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A computed tomography (CT) system, comprising a hybrid detector assembly coupled to a rotatable portion of a gantry of the CT system, the hybrid detector assembly including a plurality of detector arrays, the detector arrays separated along a direction parallel to an axis of motion of a table of the CT system, each detector array of the plurality of detector arrays including a different detector material, wherein at least one of the hybrid detector assembly and an x-ray tube of the CT system is mounted on a translation mechanism configured to allow a position of the at least one of the hybrid detector assembly and the x-ray tube to change within the rotatable portion of the gantry between a first acquisition of projection data and a second acquisition of projection data.

2. The CT system of claim 1, wherein the plurality of detector arrays includes an energy integrating (EI) detector array and a photon counting (PC) detector array.

3. The CT system of claim 1, wherein the translation mechanism includes a rail.

4. The CT system of claim 1, wherein the translation mechanism includes a locking mechanism to lock the hybrid detector assembly in a desired position during an acquisition.

5. The CT system of claim 1, further comprising a processor, and a non-transitory memory including instructions that when executed by the processor, cause the at least one of the hybrid detector assembly and the x-ray tube to move from a first position, where the x-ray tube is centered on a first detector array of the plurality of detector arrays, the first detector array used for the first acquisition of projection data, to a second position where the x-ray tube is centered on a second detector array of the plurality of detector arrays, the second detector array used for the second acquisition of projection data.

6. The CT system of claim 5, wherein the at least one of the hybrid detector assembly and the x-ray tube is moved in the direction parallel to the axis of motion of the table of the CT system.

7. The CT system of claim 5, wherein:
the first detector array is an energy integrating detector (EID) array, and a conventional CT image is generated from the first acquisition of projection data; and
the second detector array is a photon-counting computed tomography (PCCT) detector array, and an image based on PCCT data is generated from the second acquisition of projection data.

8. The CT system of claim 1, wherein a detector array of the plurality of detector arrays is selected by a user of the CT system to perform an acquisition based on at least one of:
one or more desired characteristics of an image reconstructed from projection data obtained during the acquisition;
a desired time frame for reconstructing the image; and
an amount of computing and/or memory resources available during the acquisition.

9. The CT system of claim 1, wherein the plurality of detector arrays are arranged in an adjacent manner, where each detector array of the plurality of detector arrays is in face-sharing contact with neighboring detector arrays in the hybrid detector assembly.

10. The CT system of claim 1, wherein a detector material of the different detector material cannot be manufactured with a desired extent in at least one dimension.

11. The CT system of claim 1, wherein an extent of two or more detector arrays of the plurality of detector arrays in the direction parallel to the axis of motion of the table is not equal.

12. The CT system of claim 11, wherein a first detector array of the two or more detector arrays is an energy integrating detector (EID) array, a second detector array of the two or more detector arrays is a photon-counting computed tomography (PCCT) array, and a surface area of the EID array is greater than the surface area of the PCCT array.

13. The CT system of claim 1, wherein a field of view of two or more detector arrays of the plurality of detector arrays is not equal.

14. A method for a computed tomography (CT) imaging system, the method comprising:

receiving, from a user of the CT system, a first selection of a first detector type from a plurality of detector types of the CT imaging system;
adjusting a position of a hybrid detector assembly including a plurality of detector arrays, each detector array of the plurality of detector arrays having a different detector type, from a first position within a rotatable portion of a gantry of the CT system to a second position within the rotatable portion of the gantry, the second position centering an x-ray source of the CT system on a first detector array of the first detector type;
scanning a subject using the first detector array;
reconstructing an image of the subject based on projection data acquired via the first detector array.

15. The method of claim 14, wherein the detector type is based on at least one of:
a semiconductor material of a detector array of the plurality of detector arrays;
a size of a detector element of the detector array; and
a thickness of the detector array.

16. The method of claim 14, further comprising:
receiving from the user a second selection of a second detector type from the plurality of detector types, the second detector type different from the first detector type;
adjusting the position of the hybrid detector assembly from the second position within the rotatable portion of the gantry to a third position within the rotatable portion of the gantry, the third position centering the x-ray source on a second detector array of the second detector type;
scanning the subject using the second detector array;
reconstructing the image of the subject based on projection data acquired via the second detector array.

17. The method of claim 14, wherein adjusting the position of the hybrid detector assembly further comprises:
sliding the hybrid detector assembly along a translation mechanism of the CT imaging system from the first position to the second position; and
locking the hybrid detector assembly in the second position.

18. A computed tomography (CT) imaging system, comprising:
a hybrid detector assembly coupled to a rotatable portion of a gantry of the CT system, the hybrid detector assembly including a plurality of detector arrays, the detector arrays separated along a direction parallel to an axis of motion of a table of the CT system, each detector array of the plurality of detector arrays including a different detector material;
a processor; and
a non-transitory memory including instructions that when executed by the processor, cause the CT system to:
in a first condition, where the hybrid detector assembly is in a first position, the first position centering an x-ray source of the CT system on a first detector array of the plurality of detector arrays, the first detector array having a desired detector material:
scan a subject using the first detector array, and reconstruct a first image of the subject based on projection data acquired via the first detector array; and
in a second condition, where the hybrid detector assembly is in the first position centering the x-ray source on the first detector array, the first detector array not having the desired detector material:

move the hybrid detector assembly to a second position, the second position centering the x-ray source on a second detector array, the second detector array having the desired detector material; and scan the subject using the second detector array, and reconstruct a second image of the subject based on projection data acquired via the second detector array.

19. The system of claim 18, wherein the first position and the second position are two points along a dimension parallel to the axis of motion of the table.

\* \* \* \* \*